United States Patent
Yamamoto et al.

(10) Patent No.: US 10,470,665 B2
(45) Date of Patent: Nov. 12, 2019

(54) IMAGING APPARATUS FOR DIAGNOSIS AND METHOD OF CONTROLLING THE SAME

(71) Applicant: TERUMO KABUSHIKI KAISHA, Shibuya-ku, Tokyo (JP)

(72) Inventors: Keiichiro Yamamoto, Shizuoka (JP); Isao Mori, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 884 days.

(21) Appl. No.: 15/081,332

(22) Filed: Mar. 25, 2016

(65) Prior Publication Data

US 2016/0206208 A1 Jul. 21, 2016

Related U.S. Application Data

(63) Continuation of application No. PCT/JP2013/005773, filed on Sep. 27, 2013.

(51) Int. Cl.
*A61B 5/00* (2006.01)
*A61B 1/00* (2006.01)
(Continued)

(52) U.S. Cl.
CPC ........ *A61B 5/0084* (2013.01); *A61B 1/00165* (2013.01); *A61B 1/00172* (2013.01);
(Continued)

(58) Field of Classification Search
CPC ... A61B 5/0084; A61B 5/7257; A61B 5/6852; A61B 5/0073; A61B 5/02007;
(Continued)

(56) References Cited

U.S. PATENT DOCUMENTS

2004/0173733 A1  9/2004  Korn
2007/0232891 A1  10/2007  Hirota
(Continued)

FOREIGN PATENT DOCUMENTS

JP  2007-267867 A  10/2007
JP  2013-013439 A  1/2013
(Continued)

OTHER PUBLICATIONS

Extended European Search Report dated Apr. 21, 2017 in corresponding European Patent Application No. 13894207.3 (7 pages).
(Continued)

*Primary Examiner* — Joel Lamprecht
(74) *Attorney, Agent, or Firm* — Buchanan Ingersoll & Rooney PC

(57) ABSTRACT

An imaging apparatus is disclosed for diagnosis, which can automatically discriminate an optical refractive index of flushing liquid which is utilized during pull-back scanning, and reconstruct a blood vessel cross-sectional image having an appropriate scale. An intensity of reflected light in a medium having a known refractive index is obtained in advance. An intensity of the reflected light on a border surface between a catheter sheath unit and the flushing liquid is detected based on interference light data, which is obtained during the pull-back scanning. The refractive index of the flushing liquid is calculated based on the intensity of the reflected light, an intensity of incident light obtained from the stored reflected light, and a known refractive index of the catheter sheath unit.

12 Claims, 7 Drawing Sheets

(51) Int. Cl.
*A61B 1/07* (2006.01)
*A61B 1/015* (2006.01)
*A61B 5/02* (2006.01)

(52) U.S. Cl.
CPC ............... *A61B 1/015* (2013.01); *A61B 1/07* (2013.01); *A61B 5/0066* (2013.01); *A61B 5/0073* (2013.01); *A61B 5/02007* (2013.01); *A61B 5/6852* (2013.01); *A61B 5/7257* (2013.01); *A61B 5/742* (2013.01); *A61B 2576/02* (2013.01)

(58) Field of Classification Search
CPC ....... A61B 5/742; A61B 1/015; A61B 5/0066; A61B 1/07; A61B 1/00172; A61B 1/00165; A61B 2576/02
See application file for complete search history.

(56) References Cited

U.S. PATENT DOCUMENTS

| | | |
|---|---|---|
| 2011/0222070 A1 | 9/2011 | Nagai et al. |
| 2013/0006105 A1 | 6/2013 | Furuichi |
| 2015/0245768 A1 | 9/2015 | Hasegawa et al. |

FOREIGN PATENT DOCUMENTS

| | | |
|---|---|---|
| WO | WO 2010/050296 A1 | 5/2010 |
| WO | 2013/121602 A1 | 8/2013 |

OTHER PUBLICATIONS

International Search Report (PCT/ISA/210) dated Oct. 29, 2013, by the Japanese Patent Office as the International Searching Authority for International Application No. PCT/JP2013/005773.

IMAGING APPARATUS FOR DIAGNOSIS AND METHOD OF CONTROLLING THE SAME

CROSS-REFERENCES TO RELATED APPLICATIONS

This application is a continuation of International Application No. PCT/JP2013/005773 filed on Sep. 27, 2013, the entire content of which is incorporated herein by reference.

TECHNICAL FIELD

The present disclosure relates to an imaging apparatus for diagnosis using optical interference, and a method of controlling the same.

BACKGROUND DISCUSSION

Endovascular therapy using a high-performance catheter such as a balloon catheter and a stent has been performed. An imaging apparatus for diagnosis such as an optical coherence tomography (OCT) apparatus is generally used for pre-operative diagnosis and post-operative follow-up.

The optical coherence tomography apparatus can include a built-in optical fiber in which an imaging core having an optical lens and an optical mirror is attached to a distal end thereof, and uses a probe having a sheath in which at least a distal end portion is transparent. The probe is guided to the inside of a blood vessel of a patient, and while the imaging core rotates, a blood vessel wall is irradiated with light via the optical mirror. Radial scanning is performed by receiving reflected light again from the blood vessel wall via the optical mirror, thereby constructing a cross-sectional image of the blood vessel based on the obtained reflected light. A three-dimensional image of a lumen surface of a blood vessel in a longitudinal direction can be formed by rotating the optical fiber and performing a pulling operation (generally, referred to as pulling-back) at a predetermined speed (JP-A-2007-267867). In addition, as an improved OCT, a swept-source optical coherence tomography (SS-OCT) apparatus has been developed.

Incidentally, light is attenuated and scattered in blood so that scanning of a vascular lumen surface performed by transceiving optical signals is hindered. Therefore, normally, when performing scanning, flushing liquid in which light is unlikely to be attenuated and scattered is released through a guiding catheter, and the inside of a blood vessel is filled with the flushing liquid, thereby ensuring optical transparency. The operation is literally referred to as a flushing operation. As the representative flushing liquid, there are an isotonic solution such as saline, an angiography contrast agent, and mixed liquid thereof. Here, the optical refractive index of the flushing liquid varies depending on the type, or the ratio of mixing rate.

In a case of an optical coherence tomography apparatus, light output from a light source inside the apparatus is divided into measurement light and reference light, and the measurement light is emitted toward a vascular tissue. Reflected light (scattered light) from the vascular tissue is received, and interference light with respect to the reference light reflected while being separated by a predetermined distance is obtained. Thus, a blood vessel tomographic image is reconstructed based on the intensity thereof. Therefore, in a case where the refractive index of the flushing liquid varies as described above, the space distance in liquid (calculated based on the optical path difference with respect to the reference light, and the refractive index) changes. Accordingly, the refractive index of the flushing liquid used during pull-back scanning becomes an important parameter when performing reconstruction of a blood vessel cross-sectional image.

Here, there is a case where the flushing liquid utilized when performing the pull-back scanning is forgotten, thereby resulting in problems. If proper flushing liquid can be designated, it also denotes that a proper refractive index can be designated. Therefore, it is possible to maintain a highly accurate scale (measurement) of a blood vessel cross-sectional image to be reconstructed. Meanwhile, in a case where a user erroneously designates the flushing liquid, the scale of the reconstructed blood vessel cross-sectional image becomes different from the original scale, thereby leading to an erroneous diagnosis.

SUMMARY

The present disclosure has been made in consideration of the aforementioned problems. This description aims to provide a technology of automatically discriminating the refractive index of the flushing liquid.

In accordance with an exemplary embodiment, an imaging apparatus is disclosed for diagnosis, which has a light source and a probe provided with an optically transparent catheter sheath unit which contains an imaging core emitting light from the light source toward a vascular lumen surface of a subject and detecting reflected light thereof, and that reconstructs a blood vessel image of the vascular lumen surface by executing pull-back processing in which the imaging core rotates and moves along the probe at a predetermined speed. The imaging apparatus for diagnosis includes storage means for storing information of reflected light from a border surface between a medium having a known refractive index and the catheter sheath unit when the light from the light source is emitted toward the medium having the known refractive index in a state where the probe is positioned inside the medium having the known refractive index, detection means for detecting an intensity of the reflected light from a border surface between flushing liquid used when performing pulling-back processing and the catheter sheath unit, and setting means for calculating an optical refractive index of the flushing liquid based on an intensity of light which is indicated by the information stored in the storage means, the intensity of the reflected light which is detected by the detection means, and an optical refractive index of the catheter sheath unit, and setting the calculated refractive index of the flushing liquid as a parameter for reconstructing the blood vessel image.

According to the present disclosure, a refractive index of flushing liquid is automatically calculated. Therefore, even though the type of the flushing liquid to be utilized is not particularly specified, a blood vessel image having a proper scale can be reconstructed.

In accordance with an exemplary embodiment, a non-transitory computer readable medium is disclosed containing a computer program having computer readable code embodied to carry out a method of controlling an imaging apparatus for diagnosis that has a light source and a probe provided with an optically transparent catheter sheath unit which contains an imaging core emitting light from the light source toward a vascular lumen surface of a subject and detecting reflected light thereof, and that reconstructs a blood vessel image of the vascular lumen surface by rotating the imaging core and executing transceiving of an optical signal, the method of controlling an imaging apparatus for diagnosis comprising: storing information of reflected light from a border surface between a medium having a known refractive index and the catheter sheath unit when the light from the light source is emitted toward the medium having the known refractive index in a state where the probe is positioned inside the medium having the known refractive index; analyzing data which is obtained through the transceiving of the optical signal, and detecting an intensity of reflected light from a border surface between flushing liquid used when performing the transceiving of the optical signal and the catheter sheath unit; and calculating an optical refractive index of the flushing liquid based on an intensity of light which is indicated by the stored information, the intensity of the detected reflected light, and an optical refractive index of the catheter sheath unit, and setting the calculated refractive index of the flushing liquid as a parameter for reconstructing the blood vessel image.

Other features and advantages of the present disclosure will be clearly described below with reference to the accompanying drawings. In the accompanying drawings, the same reference numerals and signs will be applied to the same or similar configurations.

BRIEF DESCRIPTION OF THE DRAWINGS

The accompanying drawings are incorporated in this description, take part in the configuration, illustrate embodiments of the present disclosure, and are used to describe the principle of the present disclosure together with the disclosure thereof.

DETAILED DESCRIPTION

Hereinafter, embodiments according to the present disclosure will be described in detail with reference to the accompanying drawings.

Figure 1:
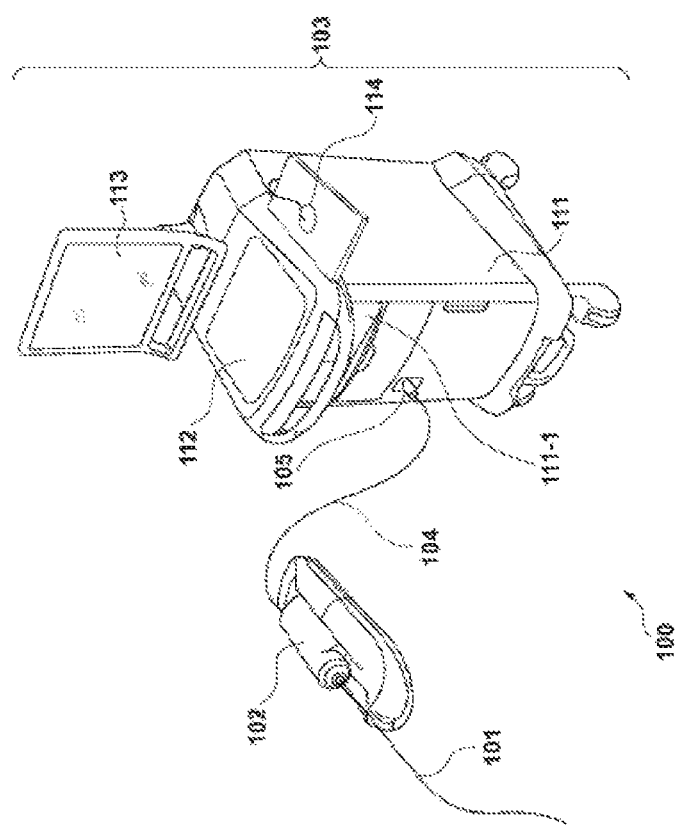
FIG. 1 is a diagram illustrating an example of the overall configuration of an imaging apparatus for diagnosis, according to an embodiment of the present disclosure.

FIG. 1 is a diagram illustrating an example of the overall configuration of an imaging apparatus 100 for diagnosis utilizing wavelength sweeping, according to an embodiment of the present disclosure.

The imaging apparatus 100 for diagnosis is configured to include a probe 101, a pull-back unit 102, and an operation control apparatus 103. The pull-back unit 102 and the operation control apparatus 103 are connected to each other through a cable 104 via a connector 105. The cable 104 contains an optical fiber and various types of signal lines.

The probe 101 contains the optical fiber in a rotatable manner. At a distal end of the optical fiber, there is provided an imaging core 250 which has an optical transceiver for transmitting light (measurement light) sent from the operation control apparatus 103 via the pull-back unit 102, in a direction in which the light travels substantially straight forward with respect to a central axis of the optical fiber, and receiving reflected light of the transmitted light from the outside (refer to FIG. 2).

The pull-back unit 102 holds the optical fiber inside the probe 101 via an adaptor which is provided in the probe 101. The optical fiber inside the probe 101 rotates by driving a motor which is built in the pull-back unit 102 so that the imaging core provided at the distal end of the pull-back unit 102 can rotate. In addition, the pull-back unit 102 also performs processing of pulling (the origin of the name of the pull-back unit) the optical fiber inside the probe 101 at a predetermined speed by driving a motor provided in a built-in linear drive unit 243 (refer to FIG. 2).

According to the above-described configuration, the probe is guided to the inside of a blood vessel of a patient, and the optical fiber inside the probe is caused to rotate by driving a radial scanning motor (the reference numeral 241 in FIG. 2) which is built in the pull-back unit 102 so that an intravascular lumen surface can be scanned around 360 degrees. Moreover, as the pull-back unit 102 causes the linear drive unit (the reference numeral 243 in FIG. 2) to pull the optical fiber inside the probe 101 at a predetermined speed, scanning along a vascular axis is performed. Consequently, a tomographic image viewed from the inside of the blood vessel can be constructed.

The operation control apparatus 103 has a function of integrally controlling the operation of the imaging apparatus 100 for diagnosis. For example, the operation control apparatus 103 is provided with a function of inputting various types of setting values into the apparatus based on user instructions, and a function of processing data which is obtained during measurement and displaying the processed data as a tomographic image inside a body cavity.

The operation control apparatus 103 is provided with a main body control unit 111, a printer & DVD recorder 111-1, an operation panel 112, and an LCD monitor 113. The main body control unit 111 generates an optical tomographic image. The reflected light obtained through measurement is caused to interfere with reference light obtained by separating light from a light source so as to generate interference light data, and processing of line data generated based on the interference light data is performed, thereby generating the optical tomographic image.

The printer & DVD recorder 111-1 prints a processing result of the main body control unit 111 and stores the processing result as data. The operation panel 112 is a user interface through which a user inputs various types of setting values and instructions. The LCD monitor 113 functions as a display apparatus. For example, the LCD monitor 113 displays a tomographic image which is generated by the main body control unit 111. The reference numeral 114 indicates a mouse which is a pointing device (a coordinate input device).

Figure 2:
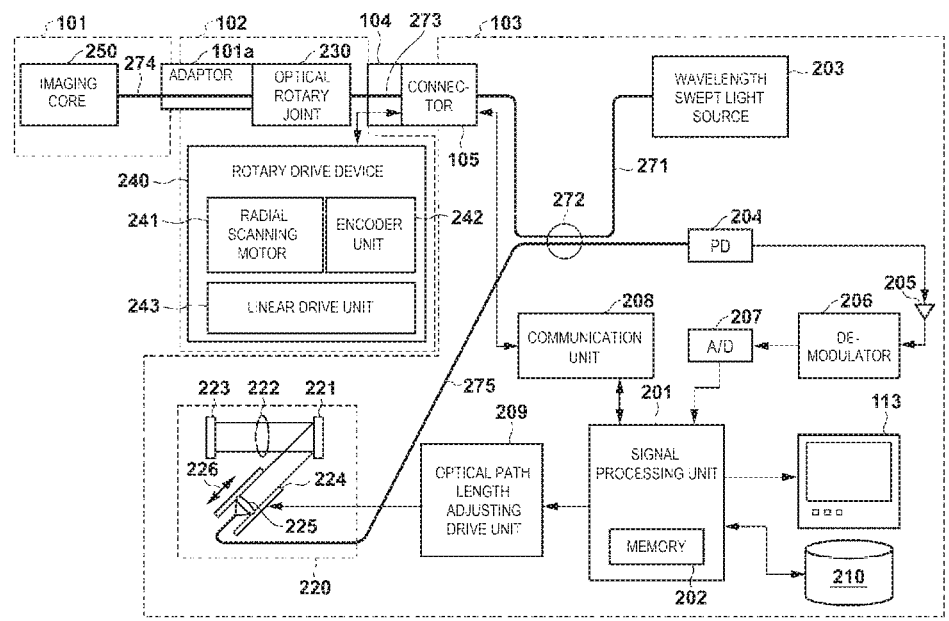
FIG. 2 is a block diagram of the configuration of the imaging apparatus for diagnosis of a first embodiment.

Subsequently, a functional configuration of the imaging apparatus 100 for diagnosis will be described. FIG. 2 is a block diagram of the configuration of the imaging apparatus 100 for diagnosis. Hereinafter, a functional configuration of a wavelength swept-type OCT will be described with reference to FIG. 2.

In the diagram, the reference numeral 201 indicates a signal processing unit which takes charge of controlling the imaging apparatus for diagnosis in its entirety and which is configured to have several circuits including a microprocessor. The reference numeral 210 indicates a non-volatile memory device which is represented by a hard disk and stores various types of programs and data files executed by the signal processing unit 201. The reference numeral 202 indicates a memory (RAM) provided inside the signal processing unit 201. The reference numeral 203 indicates a wavelength swept light source which is a light source repeatedly generating light that has a wavelength changing along a time axis within a range set in advance.

Light output from the wavelength swept light source 203 is incident on one end of a first single mode fiber 271 and is sent toward a distal side. The first single mode fiber 271 is optically coupled to a fourth single mode fiber 275 by an optical fiber coupler 272 in the middle.

The light which is emitted toward the distal side farther from the optical fiber coupler 272 in the first single mode fiber 271 is guided to a second single mode fiber 273 via the connector 105. The other end of the second single mode fiber 273 is connected to an optical rotary joint 230 inside the pull-back unit 102.

Meanwhile, the probe 101 has an adaptor 101a so as to be connected to the pull-back unit 102. The probe 101 is stably held by the pull-back unit 102 by connecting the probe 101 to the pull-back unit 102 through the adaptor 101a. Moreover, an end portion of a third single mode fiber 274 which is rotatably contained inside the probe 101 is connected to the optical rotary joint 230. As a result thereof, the second single mode fiber 273 and the third single mode fiber 274 are optically coupled to each other. The other end of the third single mode fiber 274 (a head portion side of the probe 101) is provided with the imaging core 250 which is equipped with a mirror and a lens emitting light in a direction of traveling substantially straight forward to a rotary axis (will be described in detail using FIG. 4).

As a result thereof, the light emitted from the wavelength swept light source 203 is guided to the imaging core 250 provided at an end portion of the third single mode fiber 274 via the first single mode fiber 271, the second single mode fiber 273, and the third single mode fiber 274. The imaging core 250 emits the light in a direction of traveling straight forward to the axis of the fiber and receives reflected light thereof. Then, the received reflected light is guided inversely, thereby being returned to the operation control apparatus 103.

Meanwhile, an optical path length adjustment mechanism 220 which performs fine adjustment of the optical path length of the reference light is provided at the end portion on a side opposite to the fourth single mode fiber 275 which is coupled to the optical fiber coupler 272. The optical path length adjustment mechanism 220 functions as optical path length change means for changing the optical path length corresponding to a fluctuation in the length of each probe 101 so as to be able to compensate the optical path length difference thereof in a case where the probe 101 is replaced. Therefore, a collimating lens 225 positioned at the end portion of the fourth single mode fiber 275 is provided on a one-axis stage 224 which is movable in the optical-axis direction thereof as indicated by the arrow 226.

Specifically, the one-axis stage 224 functions as the optical path length change means having a variable range of the optical path length as wide as the variability in the optical path length of the probe 101 can be absorbed in a case where the probe 101 is replaced. Moreover, the one-axis stage 224 also functions as adjustment means for adjusting an offset. For example, even in a case where the distal end of the probe 101 is not in close contact with a surface of a biological tissue, it is possible to set a state of being interfered with the reflected light from a surface position of the biological tissue by performing fine changing of the optical path length through the one-axis stage.

Light of which the optical path length is subjected to fine adjustment through the one-axis stage 224 and which is reflected by a mirror 223 via a grating 221 and a lens 222 is guided to the fourth single mode fiber 275 again and is mixed with light obtained from the first single mode fiber 271 side by the optical fiber coupler 272, thereby being received by a photo diode 204 as interference light.

The interference light received by the photo diode 204 as described above is subjected to photoelectric conversion, thereby being input to a demodulator 206 after being amplified by an amplifier 205. The demodulator 206 performs demodulation processing of extracting only a signal component of the interference light, and an output thereof is input to an A/D converter 207 as an interference light signal.

In the A/D converter 207, the interference light signal is sampled at 90 MHz at as many as 2,048 points, for example, thereby generating digital data (interference light data) for one line. The sampling frequency is set to 90 MHz on the premise that approximately 90% of a periodical cycle (25 μsec) of wavelength sweeping is extracted as the digital data at 2,048 points in a case where the repetition frequency of the wavelength sweeping is set to 40 kHz. However, the sampling frequency is not particularly limited thereto.

The interference light data generated by the A/D converter 207 in a line unit is input to the signal processing unit 201 and is temporarily stored in the memory 202. The signal processing unit 201 generates data (line data) in a depth direction by causing the interference light data to be subjected to frequency resolution through fast fourier transform (FFT). Then, the generated data is subjected to coordinate conversion so as to construct an optical cross-sectional image at each position in a blood vessel, thereby outputting the constructed image to the LCD monitor 113 at a predetermined frame rate.

The signal processing unit 201 is also connected to an optical path length adjusting drive unit 209 and a communication unit 208. The signal processing unit 201 performs controlling of the position (controlling of the optical path length) of the one-axis stage 224 via the optical path length adjusting drive unit 209.

The communication unit 208 can include several built-in drive circuits and communicates with the pull-back unit 102 while being under the control of the signal processing unit 201. Specifically, drive signals are supplied to a radial scanning motor for rotating the third single mode fiber by using the optical rotary joint inside the pull-back unit 102, signals are received from an encoder unit 242 for detecting a rotation position of the radial motor, and drive signals are supplied to the linear drive unit 243 for pulling the third single mode fiber 274 at a predetermined speed.

The above-described processing of the signal processing unit 201 is also realized as a computer executes a predetermined program.

In the above-described configuration, when the probe 101 is positioned at a blood vessel position (the coronary artery) which is a diagnostic target of a patient, flushing liquid is released inside the blood vessel through a guiding catheter in accordance with an operation of a user. The operation is performed in order to eliminate the influence of blood. When the user inputs instructions to start scanning, the signal processing unit 201 drives the wavelength swept light source 203, thereby driving the radial scanning motor 241 and the linear drive unit 243 (hereinafter, processing of irradiation and reception of light performed by driving the radial scanning motor 241 and the linear drive unit 243 will be referred to as scanning). As a result thereof, wavelength swept light is supplied to the imaging core 250 from the wavelength swept light source 203 through the above-described route. In this case, since the imaging core 250 at the position of the distal end of the probe 101 moves along the rotary axis while rotating, the imaging core 250 emits light to a vascular lumen surface and receives the reflected light thereof while rotating and moving along the vascular axis.

Figure 3:
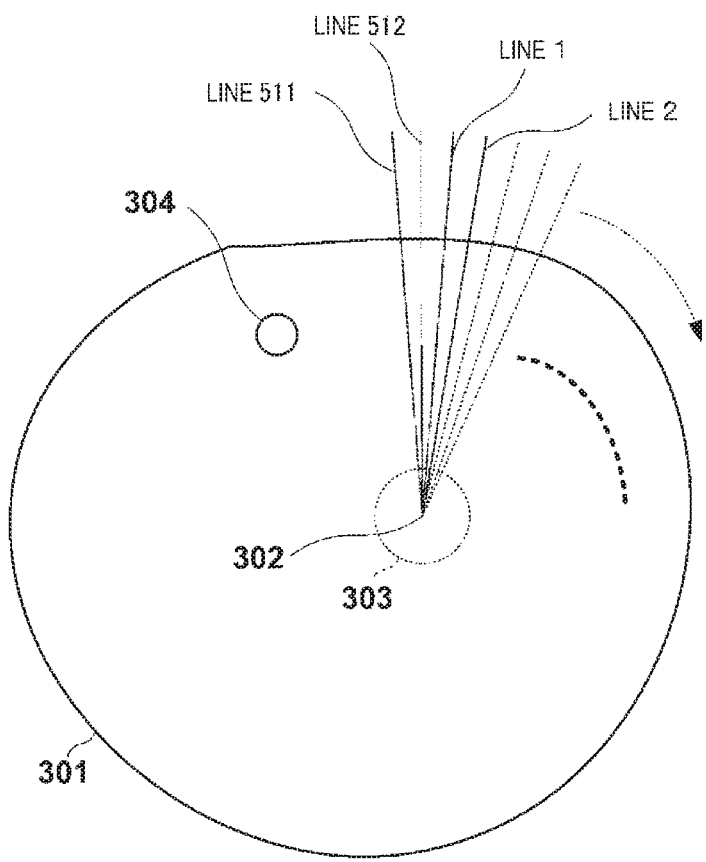
FIG. 3 is a diagram for describing intravascular radial scanning.

Here, processing related to generation of one optical cross-sectional image will be described with reference to FIG. 3. FIG. 3 is a diagram for describing reconstruction processing of a cross-sectional image of a vascular lumen surface 301 on which the imaging core 250 is positioned. The measurement light is transmitted and received multiple times while the imaging core 250 makes one rotation (360 degrees). Data of one line in a direction of light irradiation can be obtained through transceiving of light performed once. Therefore, for example, by performing transceiving of light 512 times during one rotation, 512 items of the line data radially extending from a rotary center 302 can be obtained.

Figure 4:
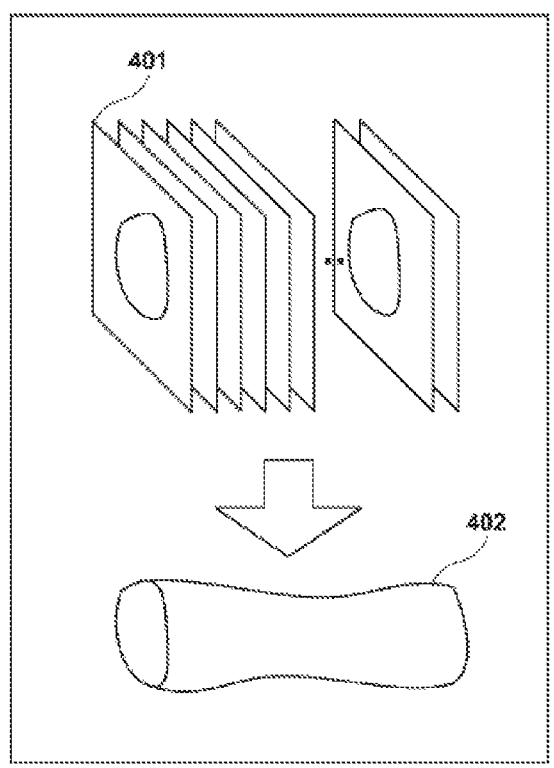
FIG. 4 is a diagram illustrating a relationship between a two-dimensional blood vessel cross-sectional image and a three-dimensional blood vessel lumen surface image.

512 items of the line data are close to one another in the vicinity of the rotary center position and are estranged from one another while being separated from the rotary center position. Therefore, pixels in the empty space of each line are generated by performing known interpolation processing so as to generate two-dimensional cross-sectional images, which can be visually recognized by a person. Generated two-dimensional cross-sectional images 401 are connected to each other in a line along the vascular axis as illustrated in FIG. 4 so that a three-dimensional blood vessel image 402 can be obtained. The center position of the two-dimensional cross-sectional images coincides with the rotary center position of the imaging core 250. However, note that, the center position thereof is not the center position of the blood vessel cross section.

In the imaging apparatus for diagnosis utilizing the wavelength sweeping, during a period of time while a certain quantity of light for one line in FIG. 3 is transmitted and received, the wavelength swept light source 203 gradually changes the wavelength of light to be output to the time axis, thereby emitting the light. Since the configuration of the wavelength swept light source 203 is known, no particular description will be given. However, the wavelength swept light source 203 outputs light within a range of the wavelength from λmax to λmin during the period of time while the light for one line is output and received. In other words, the period of λmax to λmin becomes a period for obtaining data for one line in FIG. 3 (for example, 25 μsec in the embodiment).

When transceiving light, there is a reflection caused by the surface of the lens contained in the imaging core 250, and a catheter sheath itself. Therefore, as illustrated in the diagram, several circular (concentric) shadows 303 are formed in the vicinity of the rotary central axis of the cross-sectional image. In addition, the reference numeral 304 in the diagram indicates a shadow of a guide wire which guides the probe 101 to a target lesion. The guide wire can be made from metal and is not optically transparent. Accordingly, an image of the vascular lumen surface behind the guide wire cannot be obtained when viewed from the rotary center 302. Note that, the drawings are merely conceptual diagrams.

When reconstructing the two-dimensional cross-sectional images 401 or the three-dimensional blood vessel image 402 which is obtained by connecting the images 401 to each other in a line, if the type of the utilized flushing liquid is erroneously designated, the image is reconstructed based on the erroneous refractive index inside the medium. Therefore, the scale (size) of an image to be generated becomes different from the actual scale. When performing diagnosis for arranging a stent in a blood vessel, for example, the coronary artery, the size of the diameter of the vascular lumen surface of the target lesion becomes an important factor, and thus, the erroneously designated flushing liquid cannot be ignored. According to the embodiment, the user does not designate the type of the flushing liquid. An optical refractive index inside the flushing liquid is automatically discriminated, and a parameter for reconstructing an image having a proper scale is obtained.

Figure 7:
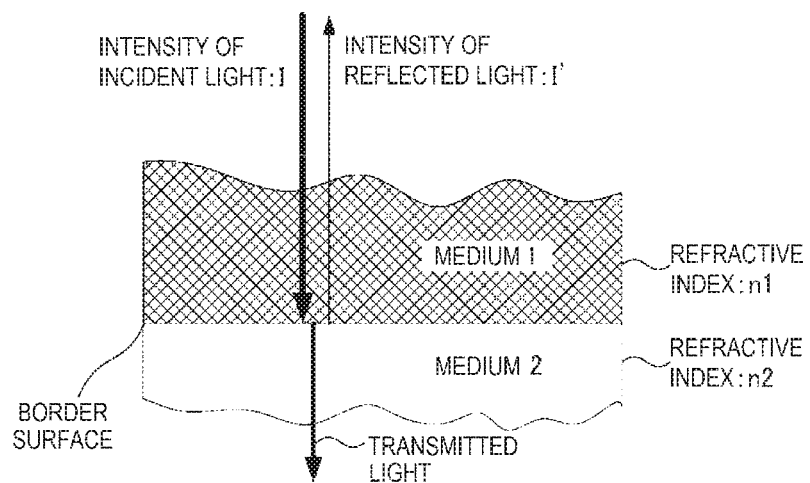
FIG. 7 is a diagram illustrating a relationship between incident light and reflected light on a border surface between mediums 1 and 2.

Here, as illustrated in FIG. 7, when I represents the intensity of light which is incident on a medium 2 having a refractive index n2 from a medium 1 having a refractive index n1 at an incident angle zero, and I' represents the intensity of the reflected light on the border surface between the two mediums 1 and 2, the relationship therebetween can be expressed as follows.

$$I'=I\times\{(n1-n2)/(n1+n2)\}^2 \quad (1).$$

Regarding the implication of the expression, the expression implies that in a case where the refractive index n1 of the medium 1 and the intensity I of the incident light are known and the refractive index n2 of the medium 2 is unknown, the refractive index n2 of the medium 2 can be obtained by measuring the intensity I' of the reflected light.

In consideration of the above-described conditions, the principle of obtaining the refractive index of the flushing liquid in the imaging apparatus 100 for diagnosis of the embodiment will be described below.

Figure 5:
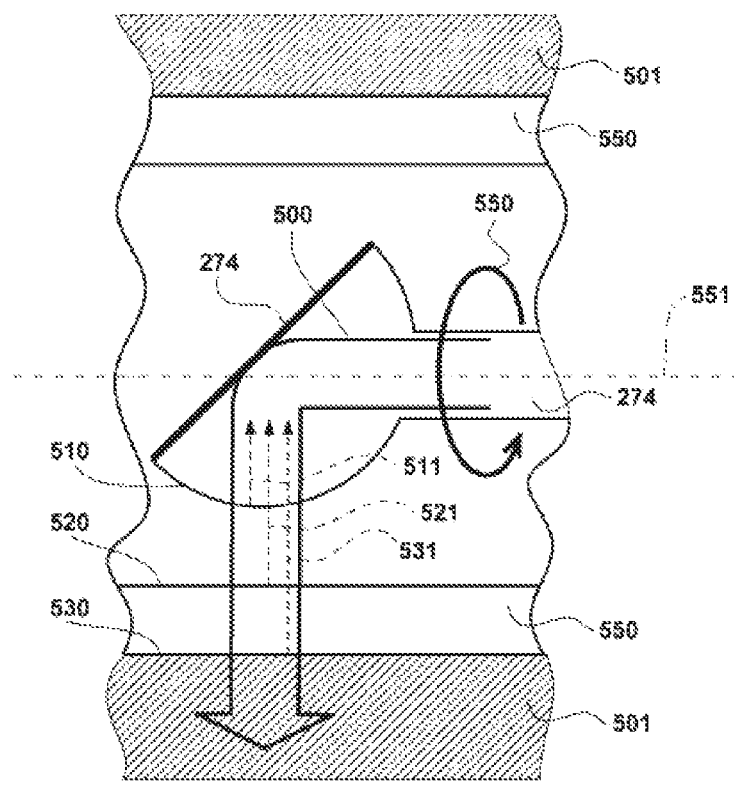
FIG. 5 is a diagram for describing the principle of detecting reflected light on a border surface between flushing liquid and a catheter sheath.
Figure 6:
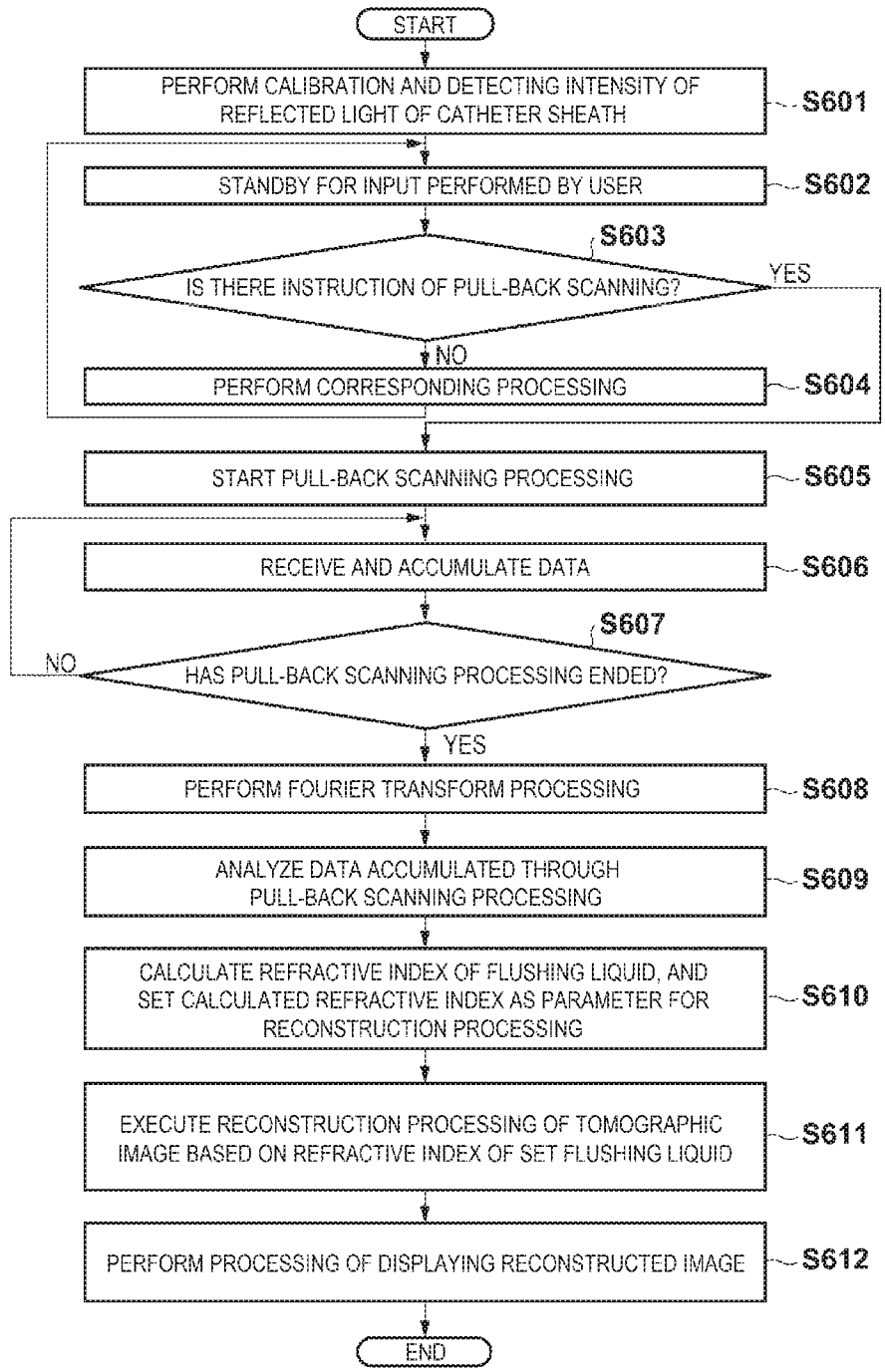
FIG. 6 is a flow chart illustrating a processing procedure of the imaging apparatus for diagnosis of the embodiment.

FIG. 5 illustrates a schematic cross-sectional view of the imaging core 250 in the vicinity of the distal end of the probe 101. As illustrated in the diagram, in the imaging core 250, an optical lens (hereinafter, a ball lens) 274a is present at the end portion of the third single mode fiber 274, the ball lens 274a rotates centering around a rotary axis 551 while transceiving optical signals, as indicated by the arrow 550 in the diagram.

The ball lens 274a has a hemispherical body shape obtained by cutting a spherical body at, for example, an angle of substantially 45 degrees with respect to the perpendicular surface of FIG. 5. A mirror portion 274b is formed on the slope thereof. In addition, the ball lens 274a also functions as a lens by having the hemispherical body shape. As described above, as indicated by the arrow 500 in the diagram, most of the light which has been incident via the pull-back unit 102 is reflected by the mirror portion 274b, and a lot of the reflected light is emitted toward the vascular lumen surface via a lens portion 510. However, in this case, even though it is modest, reflected light 511 on the surface of the lens portion 510, reflected light 521 on an inner border surface 520 of a catheter sheath 550, and reflected light 531 on an outer border surface 530 of the catheter sheath 550 are generated and are guided to the inside of the third single mode fiber 274 again. When the reflected light is measured, there is no need to rotate the third single mode fiber 274.

When transceiving the optical signals, the reference numeral 501 in the diagram is the flushing liquid. Accordingly, the reflected light 531 in the peak at a third position from a rotary central axis 551 while being subjected to scanning is considered to be the reflected light on the border surface between the catheter sheath 550 and the flushing liquid. Therefore, the refractive index of the flushing liquid 501 can be obtained based on the intensity of the reflected light 531 when the refractive index of the catheter sheath 550 and the intensity of the incident light are known.

Here, note that, even though the refractive index of the catheter sheath 550 is considered to be fixed (stored in the hard disk 210 in advance, or defined as a portion of the program), the intensity of light emitted from the wavelength swept light source 203 gradually deteriorates due to the influence of secular change, and the intensity of the reflected light on the border surface of the catheter sheath 550 fluctuates depending on the catheter. In the present embodiment, at the time of calibration of the catheter (adjustment of the optical path difference), the distal end portion of the probe 101 is positioned inside a medium such as a saline and air having the known refractive index, and the intensity I' of the reflected light which is third from the rotary center position is detected, and the result is stored in the hard disk 210. Here, the intensity I of the incident light can be obtained through the following expression.

$$I = I'/\{(n1-n2)/(n1+n2)\}^2.$$

Here, I' is an actual measurement value, n1 is the refractive index of the catheter sheath 550 (known), n2 is the known refractive index of the medium such as a saline and air (known).

In a case where scanning is actually performed, when I represents the intensity of incident light which is obtained based on the intensity of the reflected light stored in the hard disk 210, I' represents the detected intensity of the reflected light which is third from the rotary central axis 551, n1 represents the known refractive index of the catheter sheath 550, and $n_x$ represents an unknown refractive index of unknown flushing liquid, the relationship is expressed through the following expression (2) as is clear in the expression (1).

$$I' = I \times \{(n1-n_x)/(n1+n_x)\}^2 \qquad (2).$$

In the expression, the refractive index $n_x$ of the flushing liquid is the only factor which is unknown, and the refractive index $n_x$ thereof can be easily calculated.

In this manner, when the calculated refractive index $n_x$ of the flushing liquid is set as the parameter for reconstruction processing of the two-dimensional tomographic image, a two-dimensional cross-sectional image or a three-dimensional blood vessel image having the intended scale can be reconstructed. Since the image reconstruction processing itself is known, description thereof will be omitted herein.

Here, the timing for obtaining the intensity of the reflected light which is third from the rotary central axis 551 will be mentioned. The point of time starting scanning is the initial stage in which the flushing liquid is released from the distal end of the guiding catheter, and there is the possibility that not only the flushing liquid but also a certain quantity of blood is incorporated outside the catheter sheath 550. Briefly, it is not necessarily required that the reflected light on the border surface between the pure flushing liquid and the catheter sheath 550 is measured at the above-described timing. In addition, the point of time ending the scanning is the timing when blood is incorporated again in the flushing liquid so that it is not preferable to perform measurement for the same reason. In consideration of the circumstances, in accordance with an exemplary embodiment, the intermediate timing in the period from the start to the end of the scanning processing is suitable as the timing of measuring the reflected light on the border surface between the pure flushing liquid and the catheter sheath 550 so that the timing is to be utilized.

The above-described processing of the signal processing unit 201 in the imaging apparatus for diagnosis according to the embodiment can be summarized as follows.

First, in Step S601, the signal processing unit 201 executes processing of adjusting the optical path length difference between the interference light and the measurement light, that is, calibration processing before the probe 101 is inserted into a blood vessel of a patient. In this case, the processing is performed in a state where the distal end of the probe 101 is positioned inside the medium (for example, a physiological salt solution or air) having the known refractive index. Then, at that time, the intensity of the reflected light on the border surface between the outer surface of the catheter sheath 550 and the medium is measured, and the measured result is stored in the hard disk 210. When the calibration processing ends, the operation of inserting the probe 101 into a blood vessel of the patient is performed. In the meantime, the signal processing unit 201 is in a standby state waiting for an input performed by a user (Step S602).

When any input is performed by the user via the operation panel 112, in Step S603, the signal processing unit 201 performs processing of determining the input. In a case where the input is determined to be other than the instruction to start pull-back scanning, the corresponding processing is performed in Step S604. For example, this processing includes setting of the parameter regarding pulling-back such as the length to be pulled back, for example. In addition, in a case where it is determined to be the instruction to start the pulling-back, the processing proceeds to Step S605.

When an input of the instruction to start pull-back scanning is detected, in Step S605, the signal processing unit 201 drives the wavelength swept light source 203 and controls the pull-back unit 102 so as to rotate the third single mode fiber 274, thereby starting the pulling processing at a predetermined speed. As a result thereof, the interference light is received by the photo diode 204 via the optical fiber coupler 272, and the photo diode 204 converts the received light into an electrical signal and outputs the converted signal. The signal processing unit 201 temporarily stores the interference light data from the A/D converter 207 in the memory 202 in order (Step S606). The processing of storing the interference light data is repeatedly performed until it is determined to be the end timing which is set when starting the pull-back scanning in Step S607.

When the pull-back scanning ends, in Step S608, the signal processing unit 201 performs fast fourier transform (FFT) processing with respect to the interference light data which is stored in the memory 202, thereby generating data from the rotary axis (the line data) in the depth direction toward the radial direction. Then, in Step S609, multiple items of the line data positioned at the center during the period of the pull-back scanning are analyzed, and the average value of the values of the third peak from the rotary central axis is calculated. Thus, the calculated result is determined as the intensity I' of the reflected light on the border surface between the flushing liquid and the catheter sheath 550. In accordance with an exemplary embodiment, the reason for utilizing the average value of the multiple items of the line data is to reduce the influence of noise.

Thereafter, in Step S610, the signal processing unit 201 obtains the intensity I of the incident light based on the intensity of the reflection stored in the hard disk 210. Then, the refractive index $n_x$ of the flushing liquid is obtained based on the determined intensity I' of the reflection, the known refractive index n1 of the catheter sheath 550, and the intensity I of the incident light. Then, in Step S611, the obtained refractive index $n_x$ of the flushing liquid (or the propagation speed $x/n_x$ of light in the flushing liquid) is set as the parameter for the processing of generating a two-dimensional blood vessel cross-sectional image, thereby executing the reconstruction processing. Thereafter, in Step S612, the LCD monitor 113 displays the two-dimensional tomographic image or the three-dimensional tomographic image which has been reconstructed. The reconstruction processing of the blood vessel cross-sectional image and displaying of the reconstructed two-dimensional cross-sectional image itself are similar to those described above so that description thereof will be omitted.

As described above, according to the present embodiment, even though no particular attention is paid to the type of the flushing liquid used in the pull-back scanning, a proper refractive index is automatically calculated for the flushing liquid and a blood vessel tomographic image is reconstructed, and thus, the blood vessel tomographic image which matches the actual scale of the blood vessel can be reconstructed.

In the above-described embodiment, the intensity I' of the reflected light is expressed by using the expression (1). However, the following expression may be applied to express the same.

$$I'=A \times x+B$$

Here, x represents the refractive index of the flushing liquid, and A and B are constants which are set for each catheter.

When the above-described general expression is input to the signal processing unit in advance, and I' is obtained through two types of the mediums at the time of calibration, both A and B can be obtained. Therefore, the refractive index of unknown flushing liquid used afterwards can be calculated. In this case, as the two types of the mediums, for example, the cases can be considered where the outside of the sheath is air, reference liquid (saline), and the like.

In the above-described embodiment, description has been given regarding an example in which the operation of releasing the flushing liquid is performed through a manual operation of a user. However, the automated control system of the signal processing unit 201 may also be applied to the processing of releasing the flushing liquid.

In addition, in the embodiment, description has been given regarding an example of the swept-source optical coherence tomography (SS-OCT) apparatus. However, the embodiment may be applied to an OCT-type apparatus utilizing a single wavelength.

In addition, as described in the embodiment, a portion of the characteristics of the embodiment is realized by the signal processing unit 201 which is configured to include at least the microprocessor. Since the microprocessor realizes the function by executing the program, the program is naturally included in the scope of the present disclosure as well. In addition, generally, the program is stored in a computer readable storage medium such as CD-ROM, DVD-ROM, and the program is set to a reading device (a CD-ROM drive or the like) included in the computer, thereby being executable by being copied or installed in the system. Therefore, the computer readable storage medium can be included in the scope of the present disclosure as well.

The detailed description above describes an imaging apparatus for diagnosis using optical interference, and a method of controlling the same. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis that has a light source and a probe provided with an optically transparent catheter sheath unit which contains an imaging core emitting light from the light source toward a vascular lumen surface of a subject and detecting reflected light thereof, and that reconstructs a blood vessel image of the vascular lumen surface by rotating the imaging core and executing transceiving of an optical signal, the imaging apparatus for diagnosis comprising:
    storage means for storing information of reflected light from a border surface between a medium having a known refractive index and the catheter sheath unit when the light from the light source is emitted toward the medium having the known refractive index in a state where the probe is positioned inside the medium having the known refractive index;
    detection means for detecting an intensity of reflected light from a border surface between flushing liquid used when performing the transceiving of the optical signal and the catheter sheath unit; and
    setting means for calculating an optical refractive index of the flushing liquid based on an intensity of light which is indicated by the information stored in the storage means, the intensity of the reflected light which is detected by the detection means, and an optical refractive index of the catheter sheath unit, and setting the calculated refractive index of the flushing liquid as a parameter for reconstructing the blood vessel image.

2. The imaging apparatus for diagnosis according to claim 1, wherein the calculated refractive index of the flushing liquid is automatically calculated.

3. The imaging apparatus for diagnosis according to claim 2, wherein the blood vessel image can be reconstructed without specifying a type of the flushing liquid.

4. The imaging apparatus for diagnosis according to claim 1, comprising:
    a monitor for displaying a two-dimensional cross-sectional image or a three-dimensional cross-sectional image of the blood vessel image.

5. A method of controlling an imaging apparatus for diagnosis that has a light source and a probe provided with an optically transparent catheter sheath unit which contains an imaging core emitting light from the light source toward a vascular lumen surface of a subject and detecting reflected light thereof, and that reconstructs a blood vessel image of the vascular lumen surface by rotating the imaging core and executing transceiving of an optical signal, the method of controlling an imaging apparatus for diagnosis comprising:
    storing information of reflected light from a border surface between a medium having a known refractive index and the catheter sheath unit when the light from the light source is emitted toward the medium having the known refractive index in a state where the probe is positioned inside the medium having the known refractive index;
    analyzing data which is obtained through the transceiving of the optical signal, and detecting an intensity of reflected light from a border surface between flushing liquid used when performing the transceiving of the optical signal and the catheter sheath unit; and calculating an optical refractive index of the flushing liquid based on an intensity of light which is indicated by the stored information, the intensity of the detected reflected light, and an optical refractive index of the catheter sheath unit, and setting the calculated refractive index of the flushing liquid as a parameter for reconstructing the blood vessel image.

6. The method of controlling an imaging apparatus for diagnosis according to claim 5, comprising:
automatically calculating the refractive index of the flushing liquid.

7. The method of controlling an imaging apparatus for diagnosis according to claim 6, comprising:
reconstructing the blood vessel image without specifying a type of the flushing liquid.

8. The method of controlling an imaging apparatus for diagnosis according to claim 5, comprising:
displaying a two-dimensional cross-sectional image or a three-dimensional cross-sectional image of the blood vessel image on a monitor.

9. A non-transitory computer readable medium containing a computer program having computer readable code embodied to carry out a method of controlling an imaging apparatus for diagnosis that has a light source and a probe provided with an optically transparent catheter sheath unit which contains an imaging core emitting light from the light source toward a vascular lumen surface of a subject and detecting reflected light thereof, and that reconstructs a blood vessel image of the vascular lumen surface by rotating the imaging core and executing transceiving of an optical signal, the method of controlling an imaging apparatus for diagnosis comprising:

storing information of reflected light from a border surface between a medium having a known refractive index and the catheter sheath unit when the light from the light source is emitted toward the medium having the known refractive index in a state where the probe is positioned inside the medium having the known refractive index;

analyzing data which is obtained through the transceiving of the optical signal, and detecting an intensity of reflected light from a border surface between flushing liquid used when performing the transceiving of the optical signal and the catheter sheath unit; and calculating an optical refractive index of the flushing liquid based on an intensity of light which is indicated by the stored information, the intensity of the detected reflected light, and an optical refractive index of the catheter sheath unit, and setting the calculated refractive index of the flushing liquid as a parameter for reconstructing the blood vessel image.

10. The non-transitory computer readable medium according to claim 9, comprising:
automatically calculating the refractive index of the flushing liquid.

11. The non-transitory computer readable medium according to claim 10, comprising:
reconstructing the blood vessel image without specifying a type of the flushing liquid.

12. The non-transitory computer readable medium according to claim 9, comprising:
displaying a two-dimensional cross-sectional image or a three-dimensional cross-sectional image of the blood vessel image on a monitor.

* * * * *